(12) United States Patent
Heppe et al.

(10) Patent No.: US 9,629,952 B2
(45) Date of Patent: Apr. 25, 2017

(54) TERMINAL CLAMP FOR A MOISTURE SENSOR FOR MONITORING A VASCULAR ACCESS

(75) Inventors: John Heppe, St. Wendel (DE); Simone Lippert, Gemuenden am Main (DE); Andreas Wuepper, Buettelborn (DE)

(73) Assignee: Fresenius Medical Care Deutschland GmbH, Bad Homberg (DE)

( * ) Notice: Subject to any disclaimer, the term of this patent is extended or adjusted under 35 U.S.C. 154(b) by 172 days.

(21) Appl. No.: 13/588,109

(22) Filed: Aug. 17, 2012

(65) Prior Publication Data

US 2013/0072870 A1 Mar. 21, 2013

Related U.S. Application Data

(60) Provisional application No. 61/537,082, filed on Sep. 21, 2011.

(30) Foreign Application Priority Data

Sep. 21, 2011 (DE) .................. 10 2011 113 839

(51) Int. Cl.
*A61M 1/36* (2006.01)
*H01R 4/28* (2006.01)
*A61B 5/053* (2006.01)

(52) U.S. Cl.
CPC .......... *A61M 1/3656* (2014.02); *A61M 1/367* (2013.01); *A61M 1/3653* (2013.01);
(Continued)

(58) Field of Classification Search
CPC ........ A61M 5/5086; A61M 2039/1005; A61M 2039/1022; A61M 209/1022;
(Continued)

(56) References Cited

U.S. PATENT DOCUMENTS 3,097,906 A * 7/1963 Shannon ................. 439/855
4,053,135 A * 10/1977 Saliaris ............... F16K 7/063
24/129 R
(Continued)

FOREIGN PATENT DOCUMENTS

WO 99/26686 A1 6/1999
WO 2006/008866 A1 1/2006
(Continued)

OTHER PUBLICATIONS

PCT International Search Report and Written Opinion from PCT/EP2012/003518, mailed on Dec. 12, 2012.

*Primary Examiner* — Imani Hayman
*Assistant Examiner* — James D Ponton
(74) *Attorney, Agent, or Firm* — Kilyk & Bowersox, P.L.L.C.

(57) ABSTRACT

A terminal clamp for a moisture sensor to be placed on a patient's skin in order to monitor a vascular access to a patient includes first, lower and second, upper legs for clamped fixing of terminal tab of moisture sensor, rear end pieces of the legs being connected. The terminal clamp includes terminal contacts for contacting electrical contact points of terminal tab, and a guide piece having a slot-shaped cutout for receiving terminal tab. Slot-shaped cutout of guide piece is bounded laterally by two stop elements so that terminal tab is held in terminal clamp in a predetermined position, in which terminal contacts of terminal clamp contact the electrical contact points of terminal tab. Upper leg comprises a latching device, which is fixed in slot-shaped cutout in a snap-in manner when terminal clamp is closed to lock upper leg in position on lower leg.

15 Claims, 5 Drawing Sheets

(52) U.S. Cl.
CPC .............. *H01R 4/28* (2013.01); *A61B 5/0531* (2013.01); *A61B 5/0537* (2013.01); *A61M 2205/13* (2013.01); *A61M 2205/14* (2013.01); *Y10S 439/909* (2013.01)

(58) Field of Classification Search
CPC .. A61M 1/3653; A61M 1/3656; A61M 1/367; A61M 2025/024; A61B 2018/00178; A61B 5/053; A61B 5/0531; A61B 5/0537; H01R 11/24; H01R 11/22; H01R 4/40; Y10S 128/26; F16L 33/02; F16L 33/03; F16L 33/035; F16L 33/12
USPC .................. 604/6.16, 29, 111, 361; 340/604; 439/261, 268, 729; 600/386, 547
See application file for complete search history.

(56) References Cited

U.S. PATENT DOCUMENTS

| | | | | |
|---|---|---|---|---|
| 4,369,794 | A * | 1/1983 | Furler | 600/484 |
| 4,964,807 | A * | 10/1990 | Draus | 439/169 |
| 5,454,739 | A * | 10/1995 | Strand | 439/729 |
| 5,944,562 | A * | 8/1999 | Christensson | 439/729 |
| 6,062,915 | A * | 5/2000 | Costello | H01R 11/24 439/729 |
| 6,445,304 | B1 * | 9/2002 | Bandeian et al. | 340/604 |
| 2006/0166548 | A1 | 7/2006 | Williams et al. | |

FOREIGN PATENT DOCUMENTS

| | | |
|---|---|---|
| WO | 2009/075592 A1 | 6/2009 |
| WO | 2010/091852 A1 | 8/2010 |
| WO | 2010/136837 A1 | 12/2010 |

\* cited by examiner

TERMINAL CLAMP FOR A MOISTURE SENSOR FOR MONITORING A VASCULAR ACCESS

CROSS REFERENCE TO RELATED APPLICATIONS

The present application claims priority to U.S. Provisional Application Ser. No. 61/537,082, filed on Sep. 21, 2011, and claims priority to Application No. DE 10 2011 113 839.4, filed in the Federal Republic of Germany on Sep. 21, 2011, each of which is expressly incorporated herein in its entirety by reference thereto.

FIELD OF INVENTION

The present invention relates to a terminal clamp for a moisture sensor to be placed on a patient's skin in order to monitor a vascular access to a patient. Moreover, the present invention relates to an arrangement comprising the moisture sensor and the terminal clamp. Furthermore, the present invention relates to a device for monitoring a vascular access in an extracorporeal blood treatment, wherein a patient's blood is carried away from the patient via an arterial hose line which comprises an arterial cannula and is fed to the patient via a venous hose line which comprises a venous cannula, wherein the device monitoring the vascular access comprises the moisture sensor and the terminal clamp.

BACKGROUND INFORMATION

In the field of medical technology, various arrangements are known with which fluids can be withdrawn from patients or fluids can be fed to patients via a hose line. The access to the patient generally takes place with a catheter for introduction into body organs or a cannula for the puncturing of vessels. During examination or treatment, a proper access to the patient must be ensured. It is therefore necessary to monitor the patient access.

A proper access to the patient is also required particularly for extracorporeal blood treatment apparatuses which comprise an extracorporeal blood circuit. The known extracorporeal blood treatment apparatuses include for example dialysis apparatuses or cell separators, which necessitate an access to the patient's vascular system. In extracorporeal blood treatment, blood is removed from the patient with an arterial puncture cannula via an arterial hose line, the blood being fed back again to the patient with a venous puncture cannula via a venous hose line.

Moisture sensors that are placed on the patient's skin are described in International Patent Publication No. WO 2006/008866 A1 and U.S. Pat. No. 6,445,304. The moisture sensors comprise electrical contact points, at which the evaluation unit of the device for monitoring the vascular access is connected via a connection cable.

Particular demands are made on the terminal clamps for the moisture sensors for monitoring the vascular access in an extracorporeal blood treatment. The terminal clamps on the one hand must not become detached from the moisture sensor during the extracorporeal blood treatment. On the other hand, a reliable electrical contact must be ensured.

International Patent Publication No. WO 99/26686 describes an electrical terminal clamp for a sensor to be placed on the patient's skin in order to measure the electrical resistance. The known terminal clamp comprises a lower and an upper clamping jaw, there being provided on the upper clamping jaw terminal contacts which make contact with the electrical contact points of the sensor when the terminal clamp is closed. The two clamping jaws are pre-tensioned in the closed position in a spring-loaded manner by means of a spring.

SUMMARY

A problem underlying the present invention is to provide a terminal clamp for a moisture sensor for monitoring a vascular access, which can be produced cost-effectively and in large numbers and also permits reliable electrical contacting even under mechanical loads.

Moreover, a problem underlying the present invention is to make available an arrangement with such a terminal clamp and a moisture sensor for monitoring a vascular access as well as a device for monitoring a vascular access for an extracorporeal blood treatment apparatus, which comprises a moisture sensor and such a terminal clamp.

The terminal clamp according to the present invention is intended for the connection of a moisture sensor to be placed on a patient's skin, said moisture sensor comprising a terminal tab.

The terminal clamp according to the present invention comprises a first, lower leg and a second, upper leg for the clamped fixing of the terminal tab of the moisture sensor. The rear end piece of the lower leg and the rear end piece of the upper leg are connected to one another. The terminal clamp comprises terminal contacts for the purpose of making contact with the electrical contact points of the terminal tab of the moisture sensor. Depending on the exemplary embodiment of the moisture sensor, more than two terminal contacts, for example four terminal contacts, can be provided.

The terminal clamp according to the present invention is characterised by a guide piece, which comprises a slot-shaped cutout for receiving the terminal tab of the moisture sensor. The slot-shaped cutout of the guide piece is bounded laterally by two stop elements, so that the terminal tab is held in the terminal clamp in a predetermined position, in which the terminal contacts of the terminal clamp make contact with the electrical contact points of the terminal tab.

In the terminal clamp according to the present invention, the slot-shaped cutout of the guide piece serves, as it were, to lock the upper leg in position on the lower leg. The upper leg comprises a latching device, which is fixed in a snap-in manner in the slot-shaped cutout when the terminal clamp is closed. The guide piece thus serves not only to guide the terminal tab when the moisture sensor is pushed into the terminal clamp, but also to lock the two legs in position when the terminal clamp is closed.

In a preferred exemplary embodiment, the front end piece of the upper leg comprises a contact face, which faces the front end piece of the lower leg and on which the terminal contacts are disposed. The front end piece of the lower leg preferably comprises a seating face for the terminal tab, said seating face facing the front end piece of the upper leg. It is however also possible in principle for the lower leg to be constituted as a contact face and for the upper leg to be constituted as a seating face. Both legs can also be constituted as contact faces with terminal contacts, if contact points are provided both at the upper side and the lower side of the tab of the moisture sensor.

In a further preferred exemplary embodiment, the seating face for the terminal tab of the moisture sensor comprises a seating element which is made of an elastic material. The flexible seating element ensures a frictionally locked connection between the terminal contacts of the clamp and the electrical contact points of the moisture sensor. The seating element disposed on the side lying opposite the contact points of the moisture sensor compensates for possible tolerances when the legs are pressed together, so that the terminal contacts of the moisture sensor lie uniformly on the contact points of the terminal tab.

A further particularly preferred exemplary embodiment makes provision such that the front end piece of the upper leg and the front end piece of the lower leg are constituted such that the contact face and the seating face are aligned parallel with one another when the terminal clamp is closed. It is thus ensured that the terminal contacts are aligned parallel with the contact points. This can be achieved by a suitable geometry of the legs of the terminal clamp. Loose contacts are thus avoided and reliable contacting is ensured.

In a further particularly preferred exemplary embodiment, the lateral stop elements of the guide piece each comprise at the mutually opposite inner sides a bevel with which the terminal tab is centred during the introduction into the terminal clamp. The introduction of the terminal tab is thus facilitated.

Above the slot-shaped cutout, the guide piece preferably comprises a gripping piece for opening the terminal clamp. The gripping piece acts as a lever, with which the guide piece can be bent to such an extent that the guide piece of the lower leg releases the latching device of the upper leg.

The lower end pieces of the upper and lower legs are preferably in one piece, so that the terminal clamp can be produced favourably in large numbers in the injection moulding process. The one-piece embodiment of the terminal clamp as an injection-moulded part without slots or recesses has the advantage that the hose clamp can be cleaned particularly well. For example, the hose clamp can be disinfected with a dip disinfection procedure. Moreover, it is very difficult for dirt to accumulate because, in contrast with the known clamps, which comprise a plurality of elements, for example upper and lower sections, connection pieces, springs etc., slots or recesses in which dirt could easily accumulate are not present.

The rear end pieces of the upper and lower legs are preferably constituted as a connection piece, which pretensions in a spring-loaded manner the upper and lower legs in the opened position. The upper and lower legs and the connection piece are preferably constituted such that the upper and lower legs are only slightly deformed during opening and closing of the terminal clamp. Since the two legs are not deformed, it is possible to achieve a plane-parallel arrangement of the terminal contacts of the terminal clamp and the terminal points of the moisture sensor.

The rear end pieces of the upper and lower legs are preferably constituted as a connection piece with a cross-section which is essentially semicircular when the terminal clamp is opened. A terminal clamp easy to handle, which has relatively small dimensions, is thus created with a relatively straightforward geometry and relatively low mechanical stresses in the components.

The terminal clamp preferably comprises a socket for the connection of a plug of a connection cable. A plug that can be connected to the socket can however also be provided on the terminal clamp. The connection cable can however also be connected undetachably to the terminal clamp or led out from the terminal clamp.

In order to allow the terminal clamp to be gripped in a better fashion when the legs are pressed together, one of the two legs, preferably the lower leg of the terminal clamp, comprises a gripping recess. The gripping recess allows the user to grip the terminal clamp easily and to exert a targeted counterforce during opening or closing of the clamp. This thus prevents the terminal clamp from being pressed on the patient's arm during opening and closing.

The terminal contacts of the terminal clamp can be constituted differently. The contacts can comprise a convex contact face. They can also comprise contact elements pretensioned in a spring-loaded manner. Independently of the clamping force of the terminal clamp, the contact elements of the terminal contacts are thus pressed with sufficient pressing force on the contact points of the terminal tab. Any tolerances, e.g., component tolerances, geometrical tolerances, and length tolerances, are also compensated for. Terminal contacts with spring-loaded contact pins are generally known to the person skilled in the art.

Exemplary embodiments of the present invention are explained in greater detail below with reference to the accompanying drawings.

DETAILED DESCRIPTION

Figure 1:
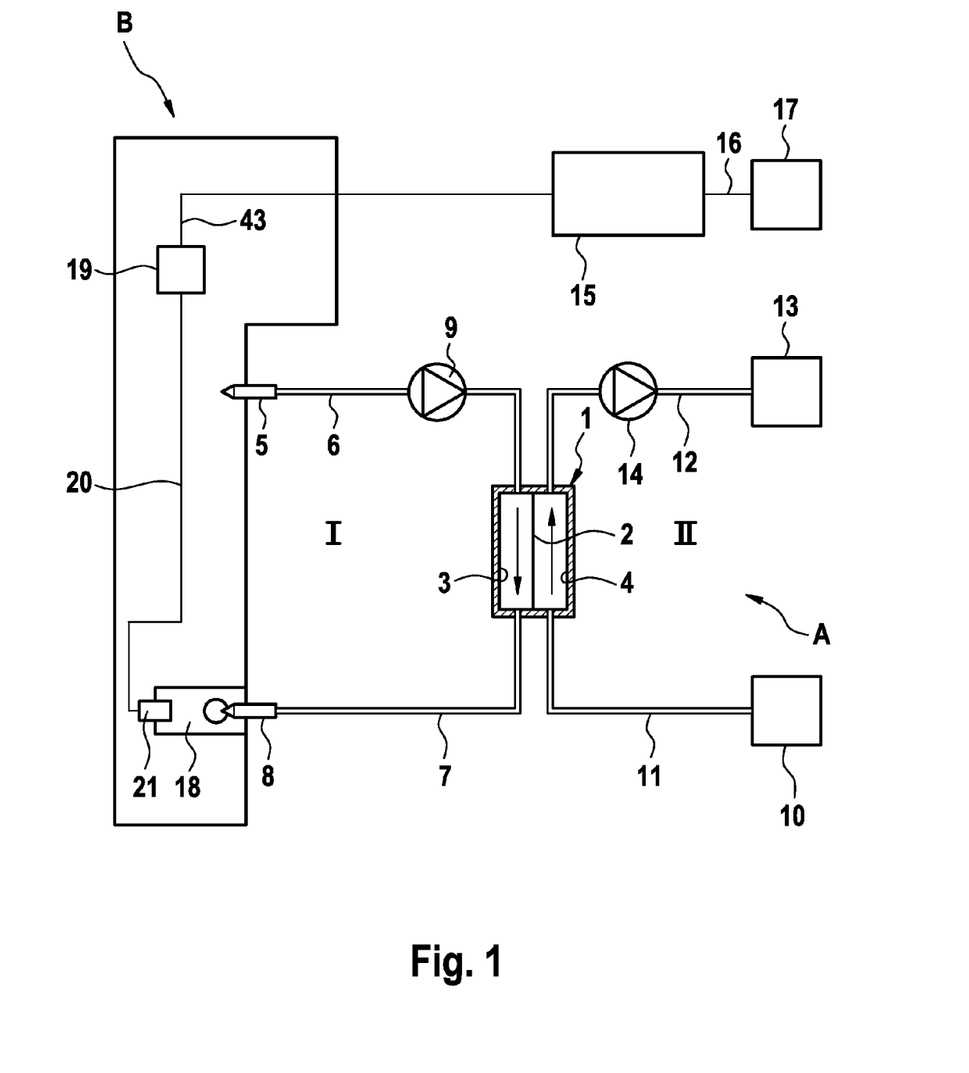
FIG. 1 shows the main components of an extracorporeal blood treatment apparatus, which comprises a device for monitoring the vascular access, according to an exemplary embodiment of the present invention.

FIG. 1 shows the main components of an extracorporeal blood treatment apparatus A, in particular a haemodialysis apparatus, which comprises a device B for monitoring the vascular access. In the present exemplary embodiment, monitoring device B is a component of haemodialysis apparatus A.

Haemodialysis apparatus A comprises a dialyser 1, which is divided by a semipermeable membrane 2 into a blood chamber 3 and a dialysing fluid chamber 4. Connected to the fistula or the shunt of the patient by means of an arterial puncture cannula 5 is an arterial hose line 6, which leads to the inlet of blood chamber 3 of dialyser 1. Leading away from the outlet of blood chamber 3 of dialyser 1 is a venous hose line 7, which is connected by means of a venous puncture cannula 8 to the fistula or the shunt of the patient. A blood pump 9, which conveys the blood in extracorporeal blood circuit I, is incorporated into arterial hose line 6.

Dialysing fluid circuit II of dialysis apparatus A comprises a dialysing fluid source 10, to which a dialysing fluid supply line 11 is connected, which leads to the inlet of dialysing fluid chamber 4 of the dialyser. Departing from the outlet of dialysing fluid chamber 4 of dialyser 1 is a dialysing fluid discharge line 12, which leads to a drain 13. A dialysing fluid pump 14 is incorporated into dialysing fluid discharge line 12.

The control of the dialysis apparatus takes place by means of a central control unit 15, which is connected via a data line 16 to an alarm unit 17.

Monitoring device B comprises a moisture sensor 18, which is placed on the patient's skin. Moisture sensor 18 is represented only diagrammatically in FIG. 1. Moreover, monitoring device B comprises an evaluation unit 19, which is connected via a connection cable 20 to moisture sensor 18. For the connection of moisture sensor 18, use is made of terminal clamp 21 represented only diagrammatically, which is described in greater detail below.

Figure 8:
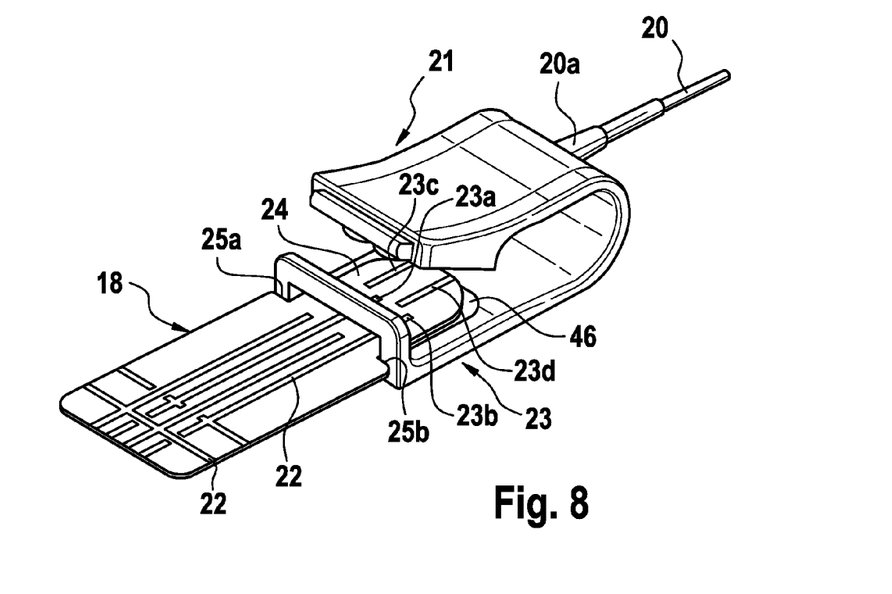
FIG. 8 shows the terminal clamp with a first embodiment of the moisture sensor, according to an exemplary embodiment of the present invention.
Figure 9:
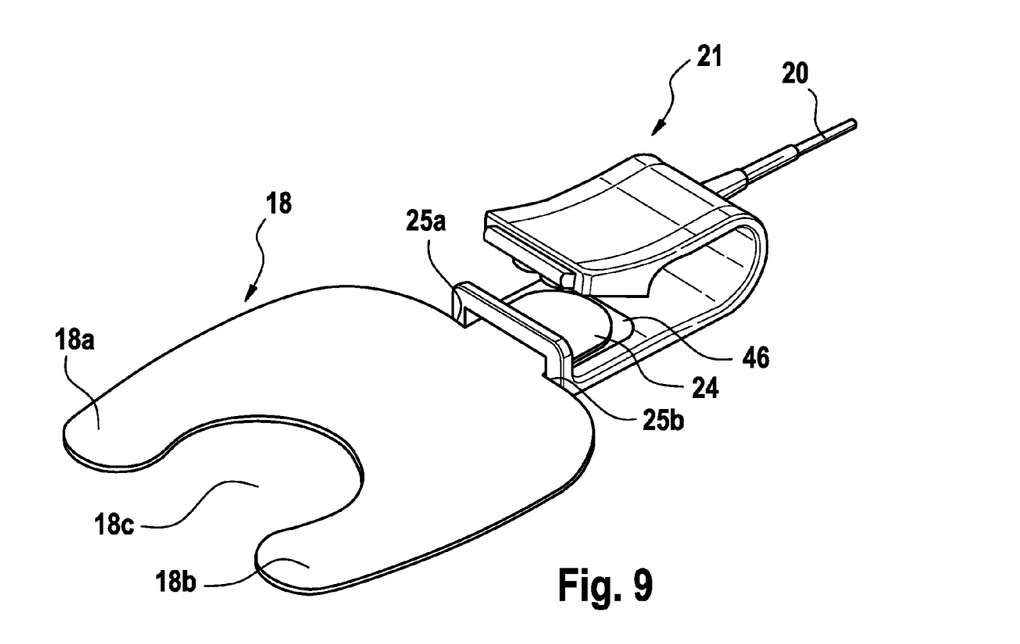
FIG. 9 shows the terminal clamp with a second embodiment of the moisture sensor, according to an exemplary embodiment of the present invention.

FIGS. 8 and 9 show terminal clamp 21 together with the moisture sensor. FIG. 8 shows a first exemplary embodiment of moisture sensor 18, whilst FIG. 9 shows a second exemplary embodiment of moisture sensor 18.

Moisture sensor 18 comprises an arrangement of strip conductors 22 represented solely by way of indication in FIG. 8, said strip conductors permitting a resistance measurement. Strip conductors 22 lead to contact points 23 in order that an electrical contact can be produced with corresponding terminal contacts of terminal clamp 21. Terminal contacts 23 are disposed on a terminal tab 24 of moisture sensor 18.

FIG. 8 shows a moisture sensor 18 with a rectangular pad which is formed integral with terminal tab 24, whilst FIG. 9 shows a moisture sensor 18 with a pad which comprises two legs 18a and 18b which surround a semicircular cutout 18c.

Terminal tabs 24 of both moisture sensors 18 have the same dimensions. In the present exemplary embodiments, two front contact points 23a and 23b as well as two rear contact points 23c and 23d are located on the upper side of terminal tab 24. The transition between the terminal tab and the pad with strip conductors 22 forms a shoulder 25a and 25b, with which moisture sensor 18 abuts against terminal clamp 21 when the terminal tab lies in the terminal clamp.

Terminal clamp 21 for moisture sensor 18 is described in detail below.

Figure 2:
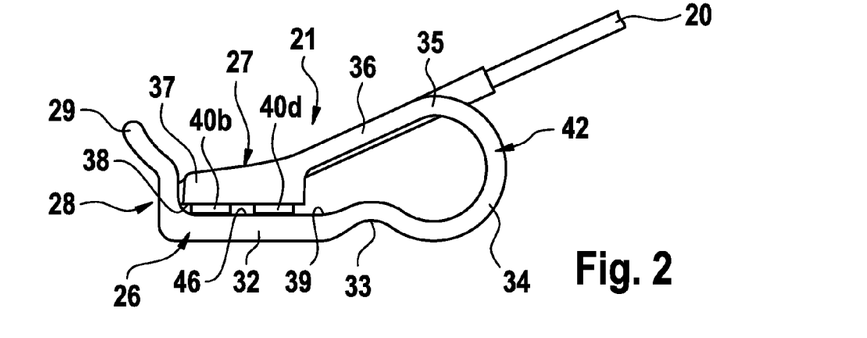
FIG. 2 shows a side view of the closed terminal clamp for the connection of the moisture sensor of the device for monitoring the vascular access, according to an exemplary embodiment of the present invention.
Figure 3:
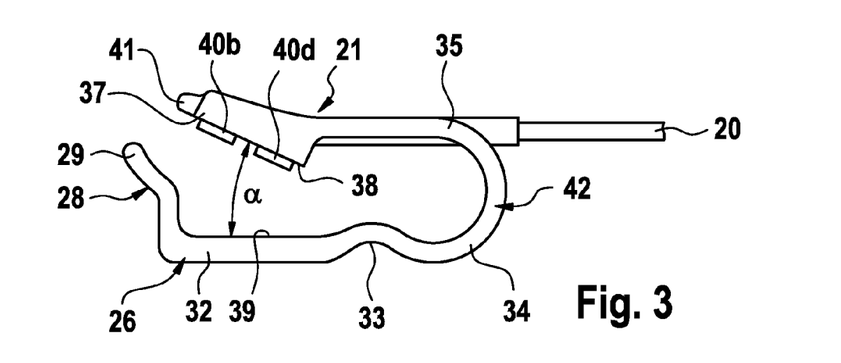
FIG. 3 shows the opened terminal clamp, according to an exemplary embodiment of the present invention.

FIG. 2 shows terminal clamp 21 in the closed position, and FIG. 3 shows terminal clamp 21 in the opened position. Terminal clamp 21 is constituted in the manner of a clip, which is produced as a one-piece injection-moulded part made of plastic. It comprises a lower leg 26 facing the patient's skin and an upper leg 27, which are in one piece. Both legs 26, 27 are flat plastic parts.

Figure 6:
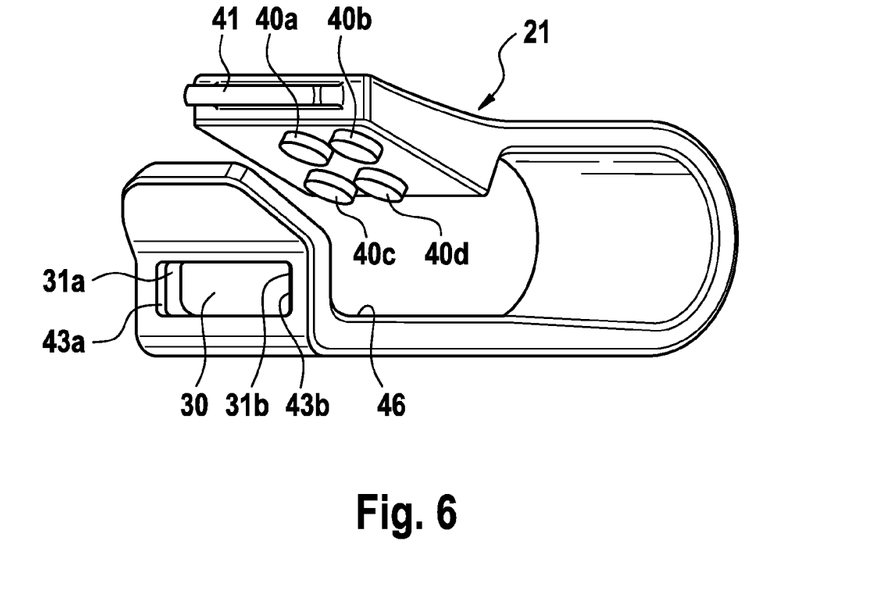
FIG. 6 shows the side view of the terminal clamp in a perspective representation, according to an exemplary embodiment of the present invention.

The front end piece of lower leg 26 is constituted as guide piece 28 for receiving terminal tab 24 of moisture sensor 18. Guide piece 28 comprises a slot-shaped cutout 30, which extends over the width of terminal clamp 21 (FIG. 6). The lateral limits of slot-shaped cutout 30 form stop elements 31a and 31b for shoulders 25a and 25b of moisture sensor 18.

Formed integrally at the upper end of guide piece 28 is a gripping piece 29, which extends obliquely upwards. Lower leg 26 comprises a straight middle leg piece 32, which follows on from guide piece 28. A gripping recess 33 is formed in middle leg piece 32. Middle leg piece 32 is bent upwards at a rear end piece 34. Rear end piece 34 of lower leg 26 is followed by downwardly bent rear end piece 35 of upper leg 27, which transforms into a straight middle leg piece 36. Front end piece 37 of upper leg 27 is positioned obliquely upwards with respect to middle leg piece 36 when terminal clamp 21 is opened.

In the closed state of terminal clamp 21, front end piece 37 of upper leg 27 comprises a plane contact face 38 facing lower leg 26, whilst middle leg piece 32 of lower leg 26 comprises a plane seating face 39 facing contact face 38 of upper leg 27. In the opened state of terminal clamp 21, contact face 38 and seating face 39 form an angle α, which amounts to 25° in the present exemplary embodiment.

Terminal contacts 40 of terminal clamp 21 are disposed on contact face 38. In the present exemplary embodiment, terminal clamp 21 comprises two front and two rear terminal contacts, which are disposed at the same distance from one another as contact points 23a to 23d of moisture sensor 18. The terminal contacts are disposed in a front and a rear row, wherein the two terminal contacts 40a, 40b of the front row are disposed offset from the two terminal contacts 40c, 40d of the rear row. The four terminal contacts 40a to 40d thus lie on the corners of an imaginary diamond. The advantage of this arrangement lies in the fact that the contact areas of the terminal contacts can be constituted as large as possible with the given space provision on the clamp. For example, the diameter of the contact areas can amount in each case to 4 mm, wherein the distance between the contacts of a row can amount to around 2.5 mm. If the contacts all lay in a row beside one another, the clamp would have to be designed much wider. If the two rows were not disposed offset, the clamp would have to be designed longer. In contrast, the clamp according to the present invention is particularly compact and cost-effective.

Figure 5:
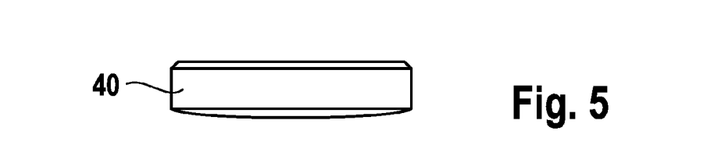
FIG. 5 shows a terminal contact of the terminal clamp, according to an exemplary embodiment of the present invention.

FIG. 5 shows one of terminal contacts 40 in a side view. The terminal contacts comprise at the underside a convex contact area, which permits reliable contacting. Instead of the terminal contacts shown in FIG. 5, however, contact pins pretensioned in a spring-loaded manner can also be provided. Such terminal pins are known to the person skilled in the art as "spring-loaded contact pins."

In the opened position of terminal clamp 21 (FIG. 3), in which terminal clamp 21 is mechanically relaxed, contact face 38 and seating face 39 are orientated in such a way that, when terminal clamp 21 is closed, i.e., tensioned (FIG. 2), contact face 38 is disposed parallel to seating face 39 and terminal contacts 40a to 40d are disposed parallel to seating face 39. Connected to terminal contacts 40a to 40d are the electrical lines of connection cable 20, which is led out of rear end piece 35 of terminal clamp 21.

Front end piece 37 of upper leg 27 comprises a latching device 41, which engages in slot-shaped cutout 30 in a snap-in manner in the closed position of terminal clamp 21 (FIG. 2), when upper leg 27 and lower leg 26 are pressed together, so that the upper leg cannot spring back into the opened position (FIG. 3). The latching device is a latching nose 41 extending over the width of slot-shaped cutout 30.

In order to compensate for tolerances, a flexible seating element 46 made from an elastic material, on which terminal tab 24 of moisture sensor 18 rests, is provided on seating face 39 of lower leg 26 of terminal clamp 21.

Terminal clamp 21 is constituted such that connection piece 42 of lower and upper leg 26, 27 has an essentially semicircular cross-section. Connection piece 42 acts as a torsion spring for lower and upper leg 26, 27, wherein connection piece 42, in contrast with legs 26, 27, becomes slightly deformed during the opening or closing of the clamp. A deformation of legs 26, 27 would be disadvantageous for the desired plane-parallel contact pressure of the terminal contacts when the terminal clamp is closed. In order to displace the deformation always into the region of connection piece 42 during the opening or closing of the clamp, the connection piece can be weakened in its cross-section at least over a part of its length.

The radius of connection piece 42 remains almost unchanged during the closing of the terminal clamp. Even when the clamp is closed, connection piece 42 exerts a spring force on the two legs 26, 27, which however is taken up by latching device 41. When latching device 41 is released, the spring force of connection piece 42 leads to the opening of the terminal clamp until the connection piece is mechanically relaxed. A handling advantage arises from the fact that the terminal clamp, during stripping down, for example after completion of the dialysis treatment, automatically opens after the release of the latching device, and the clamp can thus be removed particularly easily from the tab of the sensor.

For the connection of moisture sensor 18 to the evaluation unit of monitoring device B, terminal tab 24 of moisture sensor 18 is pushed into slot-shaped cutout 30 of guide piece 28 of terminal clamp 21 until stop elements 31a and 31b of guide piece 28 strike against shoulders 25a, 25b of moisture sensor 18. Both legs 26, 27 of terminal clamp 21 are then pressed together until latching device 41 latches into slot-shaped cutout 30 (FIG. 2).

Lateral stop elements 31a, 31b of guide piece 28 each comprise at the mutually opposite sides a bevel 43a, 43b (FIG. 6), which serves to centre terminal tab 24 of moisture sensor 18 when the terminal tab is pushed into the slot-shaped cutout of guide piece 28. The width of terminal tab 24 and the width of slot-shaped cutout 30 are dimensioned such that terminal tab 24 exactly fits into guide piece 28.

Figure 4:
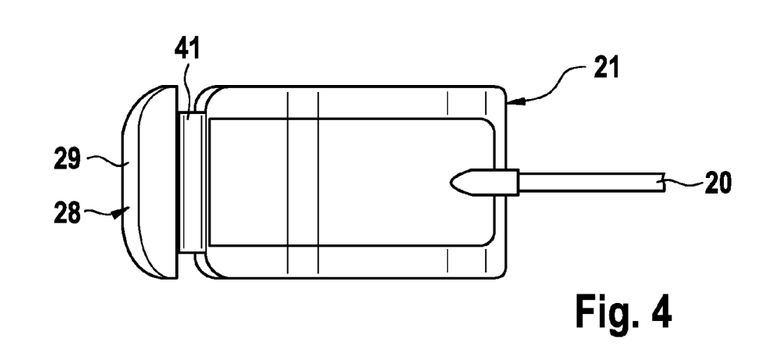
FIG. 4 shows the terminal clamp in plan view, according to an exemplary embodiment of the present invention.

Connection cable 20 can be fixedly connected to terminal clamp 21 (FIGS. 2 to 4). It is however also possible for the connection cable to comprise at one end a plug 20a, which is pushed into a matching socket 44, which is provided on terminal clamp 21 (FIG. 7).

Figure 7:
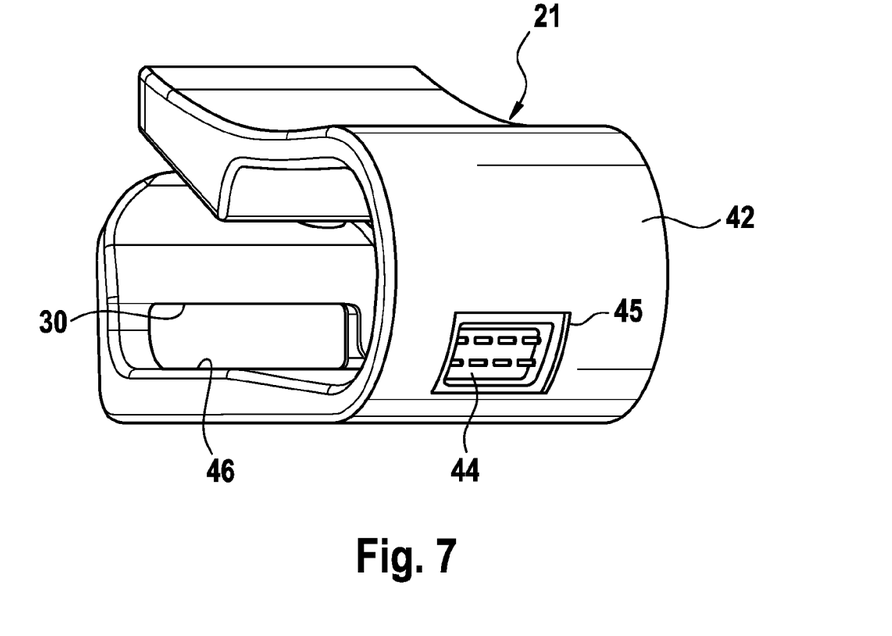
FIG. 7 shows a perspective representation of the terminal clamp in a rear view, according to an exemplary embodiment of the present invention.

FIG. 7 shows an exemplary embodiment of terminal clamp 21, wherein socket 44 is disposed in a recess 45 of connection piece 42 of the two legs 26, 27. FIGS. 8 and 9 show an exemplary embodiment, wherein the cable is connected undetachably to the clamp, i.e., a socket is not provided.

Plug 20a and socket 44 can be configured in such a way that plug 20a becomes detached from socket 44 when a predetermined tensile force on connection cable 20 is exceeded, so that plug 20a and socket 44 act as a predetermined breaking point. This has the advantage that inadmissible tensile forces on connection cable 20 cannot be transferred via the terminal clamp and the moisture sensor to the vascular access and/or the patient's skin at the vascular access. Pulling-out of plug 20a from socket 44 is detected by evaluation unit 19.

When the terminal clamp is being closed, it must be ensured that contact points 23a to 23d of moisture sensor 18 are exactly aligned on terminal contacts 40a to 40d of terminal clamp 21.

Figure 10:
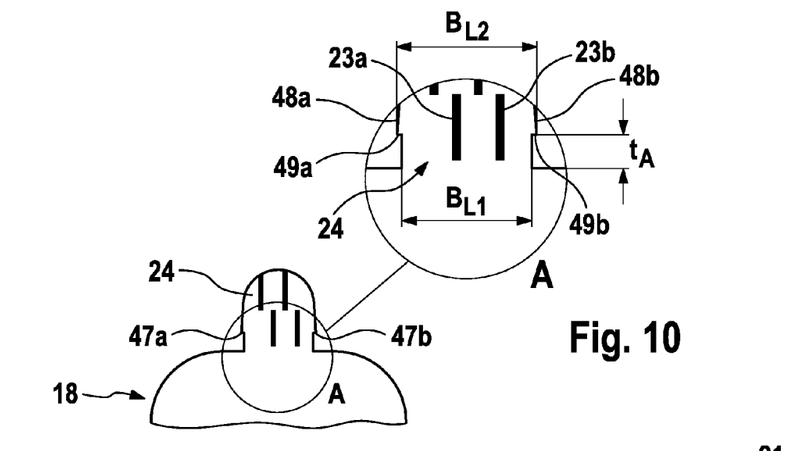
FIG. 10 shows the terminal tab of a further embodiment of the moisture sensor, according to an exemplary embodiment of the present invention.

FIG. 10 shows terminal tab 24 of an alternative exemplary embodiment of moisture sensor 18, which differs from the exemplary embodiment described by reference to FIG. 9 in that tab 24 can be pushed in a snap-in manner into slot-shaped recess 30 of terminal clamp 21, the tab being secured against twisting in the terminal clamp. The parts corresponding to one another are provided with the same reference numbers.

Figure 11:
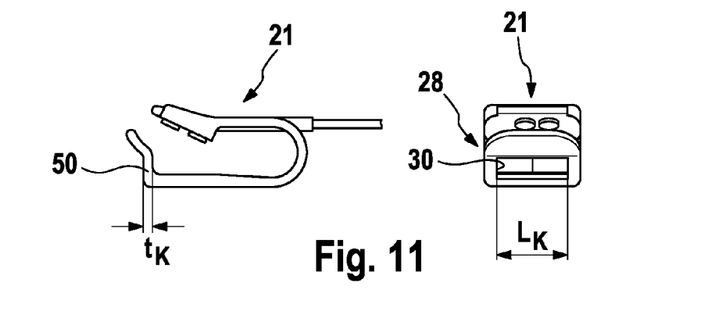
FIG. 11 shows the terminal clamp for the moisture sensor of FIG. 10 in a side and front view, according to an exemplary embodiment of the present invention.

Tab 24 of moisture sensor 18 comprises at both longitudinal sides a snap-in hook 47a, 47b with a front bevel 48a, 48b and a rear heel 49a, 49b. In FIG. 10, the width of tab 24 at the narrowest point is denoted by $B_{L1}$ and at the broadest point by $B_{L2}$, whilst the distance between heel 49a, 49b and stop 25a, 25b of moisture sensor 18 is denoted by $t_4$. The width of slot-shaped recess 30 of guide piece 28 of terminal clamp 21 is denoted by $L_K$ in FIG. 11. Clamp 21 comprises a stop 50 with width $t_K$ on guide piece 28. $B_{L1}<L_K<B_{L2}$ and $t_4>t_K$ must apply for the correct snapping into position of the tab in the clamp, the dimensional difference between $B_{L2}$ and $L_K$ being able to be kept very small from the production standpoint. The difference between $B_{L2}$ and $L_K$ is greatly dependent on the elasticity of the material of the tab, the tab preferably comprising a textile fabric which becomes elastically deformed when tab 24 is introduced into recess 30 of clamp 21. The force for the deformation of tab 24 at bevel 48a, 48b first increases linearly, after which it then declines again abruptly at heel 49a, 49b, which is clearly discernible as snapping-into position.

Figure 12:
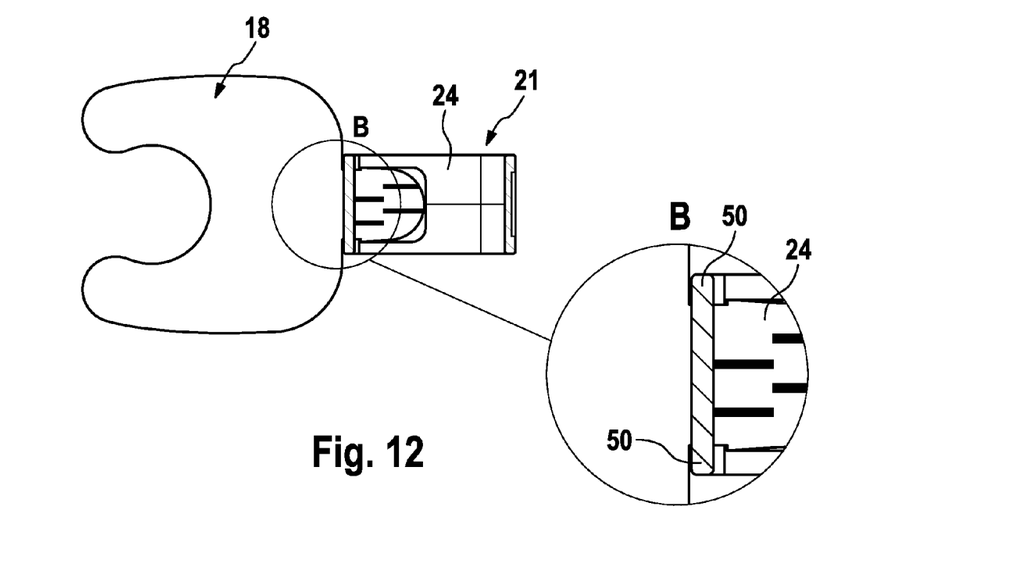
FIG. 12 shows the terminal tab of the moisture sensor of FIG. 10 inserted into the terminal clamp of FIG. 11, according to an exemplary embodiment of the present invention.

After the insertion of tab 24, moisture sensor 18 is also secured against twisting, since tab 24 strikes against stop 50 of terminal clamp 21 when heel 49a, 49b is rotated. FIG. 12 shows that the tab is fixed secure against twisting in the terminal clamp on account of the positive-locking fit when contact points and terminal contacts are correctly aligned. A maximum possible twisting angle can be set with the condition $t_4/t_K>1$ and $B_{L1}/L_K<1$, the quotient preferably being selected such that snapping into position remains discernible.

The particular exemplary embodiment of the moisture sensor has the advantage that the sensor cannot be unintentionally detached even when the terminal clamp is opened. This is advantageous when sensor and clamp are fitted together before the treatment or when the opened clamp and the moisture sensor are released shortly before the start of treatment in order for example to carry out needle fixing or to insert gauze.

What is claimed is:

1. A terminal clamp for a moisture sensor to be placed on a patient's skin in order to monitor a vascular access, the moisture sensor comprising a flat terminal tab on which electrical contact points are disposed, the terminal clamp comprising:
    a lower leg and an upper leg, a rear end piece of the lower leg and a rear end piece of the upper leg being connected; and
    terminal contacts configured to contact the electrical contact points of the flat terminal tab of the moisture sensor;
    wherein a front end piece of the upper leg comprises a latching device, and a front end piece of the lower leg is configured as a guide piece comprising a slot-shaped through-hole cutout configured to receive the flat terminal tab of the moisture sensor and the latching device, wherein the front end piece of the lower leg extends from a portion of the lower leg having a top surface in a plane which is below a plane of the flat terminal tab when received into the slot-shaped through-hole cutout, said slot-shaped through-hole cutout being bounded laterally by two stop elements, wherein:
the upper leg comprises a contact face which faces the front end piece of the lower leg, and on which the terminal contacts are disposed, and the front end piece of the lower leg comprises a seating face for the flat terminal tab of the moisture sensor, said seating face facing the front end piece of the upper leg, or the lower leg comprises a contact face which faces the front end piece of the upper leg, and on which the terminal contacts are disposed, and the front end piece of the upper leg comprises a seating face for the terminal tab of the moisture sensor, said seating face facing the front end piece of the lower leg, wherein the latching device and the guide piece are configured such that the latching device is fixed in a snap-in manner in the slot-shaped through-hole cutout when the flat terminal tab is received into the slot-shaped cutout and the terminal clamp is closed, and wherein the lower leg and the upper leg are configured such that the contact face and the seating face are pressed together to clamp the flat terminal tab between the contact face and the seating face to provide a contact pressure for the terminal contacts when the flat terminal tab is received into the slot-shaped through-hole cutout and the terminal clamp is closed, wherein above the slot-shaped through-hole cutout, the guide piece comprises a gripping piece configured to open the terminal clamp, wherein the upper leg, the latching device, the lower leg, and the gripping piece are formed in one piece.

2. The terminal clamp according to claim 1, wherein the seating face for the flat terminal tab of the moisture sensor comprises a seating element made from an elastic material.

3. The terminal clamp according to claim 1, wherein the front end piece of the upper leg and the front end piece of the lower leg are configured such that the contact face and the seating face are aligned parallel with one another when the terminal clamp is closed.

4. The terminal clamp according to claim 1, wherein the lateral stop elements of the guide piece each comprise at mutually opposite sides a bevel configured to center the flat terminal tab.

5. The terminal clamp according to claim 1, wherein the terminal contacts comprise a convex contact face.

6. The terminal clamp according to claim 1, wherein the lower leg comprises a gripping recess.

7. The terminal clamp according to claim 1, wherein the rear end pieces of the upper and lower legs are integrated in one piece.

8. The terminal clamp according to claim 1, wherein the rear end pieces of the upper and lower legs are configured as a connection piece which pretensions in a spring-loaded manner the upper and lower legs in an open position.

9. The terminal clamp according to claim 8, wherein the upper and lower legs and the connection piece are configured such that the upper and lower legs are one of (i) not deformed and (ii) only slightly deformed, when the terminal clamp is opened and closed.

10. The terminal clamp according to claim 8, wherein the connection piece has a cross-section which is essentially semicircular.

11. The terminal clamp according to claim 1, wherein the upper and lower legs of the terminal clamp are configured as flat parts made of plastic.

12. The terminal clamp according to claim 1, further comprising:
a socket configured to connect a plug of a connection cable.

13. An arrangement, comprising:
a moisture sensor to be placed on a patient's skin, the moisture sensor comprising a flat terminal tab on which electrical contact points are disposed; and
the terminal clamp according to claim 1;
wherein widths of the flat terminal tab and of the slot-shaped through-hole cutout of the guide piece are dimensioned such that the flat terminal tab can be pushed in a matching manner into the guide piece.

14. The arrangement according to claim 13, wherein the flat terminal tab comprises at both sides a shoulder, which rests against the stop elements of the guide piece when the flat terminal tab is pushed into the guide piece.

15. A device for monitoring a vascular access for an extracorporeal blood treatment apparatus, wherein a patient's blood is carried away from a patient via an arterial hose line having an arterial cannula and is fed to the patient via a venous hose line having a venous cannula, the device comprising:
a moisture sensor configured to be placed on the patient's skin and comprising a flat terminal tab, on which electrical contact points are disposed; and
an evaluation unit configured to be connected via a connection cable to the moisture sensor;
wherein the connection cable configured to connect to the moisture sensor comprises the terminal clamp according to claim 1.

* * * * *